US010265278B2

(12) United States Patent
Javitt

(10) Patent No.: US 10,265,278 B2
(45) Date of Patent: Apr. 23, 2019

(54) PHARMACEUTICAL COMPOSITIONS AND METHODS UTILIZING A D-AMINO ACID

(71) Applicant: AAS, LLC, Wilmington, DE (US)

(72) Inventor: Daniel Javitt, Wilmington, DE (US)

( * ) Notice: Subject to any disclaimer, the term of this patent is extended or adjusted under 35 U.S.C. 154(b) by 0 days.

(21) Appl. No.: 15/436,901

(22) Filed: Feb. 20, 2017

(65) Prior Publication Data

US 2017/0157066 A1    Jun. 8, 2017

Related U.S. Application Data

(63) Continuation of application No. 12/350,901, filed on Jan. 8, 2009, now abandoned.

(30) Foreign Application Priority Data

Jan. 8, 2008 (IL) .......................... 188681

(51) Int. Cl.
| | |
|---|---|
| *A61K 31/133* | (2006.01) |
| *A61K 31/198* | (2006.01) |
| *A61K 31/355* | (2006.01) |
| *A61K 31/375* | (2006.01) |
| *A61K 31/145* | (2006.01) |

(52) U.S. Cl.
CPC .......... *A61K 31/133* (2013.01); *A61K 31/145* (2013.01); *A61K 31/198* (2013.01); *A61K 31/355* (2013.01); *A61K 31/375* (2013.01)

(58) Field of Classification Search
None
See application file for complete search history.

(56) References Cited

U.S. PATENT DOCUMENTS

| | | | | | |
|---|---|---|---|---|---|
| 6,162,827 | A  * | 12/2000 | Javitt | ..................... | A61K 31/16 514/561 |
| 6,228,875 | B1 * | 5/2001 | Tsai | ..................... | A61K 31/198 514/380 |
| 6,420,351 | B1 * | 7/2002 | Tsai | ..................... | A61K 31/198 514/114 |
| 2002/0010212 | A1 | 1/2002 | Javitt | | |
| 2002/0013364 | A1 | 1/2002 | Javitt | | |
| 2002/0161048 | A1 | 10/2002 | Javitt | | |
| 2002/0183390 | A1 | 12/2002 | Javitt | | |
| 2003/0212262 | A1* | 11/2003 | Connolly | ................ | C12N 9/90 536/23.2 |
| 2004/0157926 | A1 | 8/2004 | Heresco-Levy et al. | | |
| 2005/0032708 | A1 | 2/2005 | Bush et al. | | |
| 2005/0159488 | A1 | 7/2005 | Javitt | | |
| 2006/0073192 | A1 | 4/2006 | Friesen et al. | | |
| 2009/0176715 | A1 | 7/2009 | Javitt | | |

FOREIGN PATENT DOCUMENTS

| | | |
|---|---|---|
| WO | 99/52519 | 10/1999 |
| WO | 01/026642 | 4/2001 |
| WO | WO 0126642 * | 4/2001 |
| WO | 04/028474 | 4/2004 |
| WO | 04/066988 | 8/2004 |
| WO | 02/36098 | 5/2005 |
| WO | 06/116353 | 11/2006 |
| WO | 07/019549 | 2/2007 |

OTHER PUBLICATIONS

Office Action from European Patent Office on Application No. EP 09701236.3, dated Oct. 17, 2012, 3 pages.
Japanese Unexamined Patent Publication (Kokai) No. JP 2003-289828 (machine translation provided at EPO website), 14 pages.
Office Action for Japanese Patent Application No. JP 2010-541882 (English translation provided by Wolff Bergman and Goller), dated Jun. 27, 2013, 3 pages.
Search of Pubmed database for publications referring in the title to agents that protect against nephrotoxicity. Search conducted at www.ncbi.nlm.nih.gov/pubmed on Jan. 20, 2016, 62 pages.
Ali et el., "Comparative protective effect on N-acetyl cysteine and tetramethylpyrazine in rafts with gentamicin nephrotoxicity" J Appl Toxicol. May 2009:29(4)302-7.
Atkuri et al., "N-Acetylcysteine—a safe antidote for cysteine/ glutathione deficiency", Science Direct, 2007, 7:355-359.
Berk et al., "N-acetyl cysteine as a glutathione precursor for schizophrenia—a double-blind, randomized, placebo-controlled trial", Biol Psychiatry, Sep. 1, 2008;64(5): pp. 361-368.
Corcoran et al., "Role of Glutathione in Prevention of Acetaminophen-Induced Hepototoxicity by N-Acetyl-L-Cysteine in Vivo: Studies with N-Acetyl-D-Cysteine in Mice", The Journal of Pharmacology and Experimental Theraputics, 1986, vol. 238, No. 1, pp. 54-61.
Ganote et al., "The nature of D-serine-induced nephrotoxicity", Am J Pathol, Nov. 1974;77(2):269-82.
Kaltenbach et al., "Renal Tubular Necrosis Induced by Compounds Structurally Related to D-Serine", Experimental and Molecular Pathology 1979, 30 pp. 209-214.
Kanter, "Comparison of oral and i.v. acetylcysteine in the treatment of acetaminophen poisoning", Am J Health-Syst Pharm, Oct. 2006, vol. 63, pp. 1821-1827.
Konno et al., "Mutant mice and rats lacking D-amino acid oxidase". Chem Biodivers. Jun. 2010;7(6):1450-8.
Krug, et al., "Why is D-serine nephrotoxic and alpha-aminoisobutyric acid protective?" Am J Physiol renal Physiol 2007, 293: pp. F382-F390.
Labrie et al., "The involvement of the NMDA receptor D-serine/ glycine site in the pathophysiology and treatment of schizophrenia", Neurosci Biobehav Rev. Mar. 2010;34(3):351-72. doi; 10.1016/j. neubiorev.2009.08.002.Epub Aug. 18, 2009.
Maekawa et al., "D-Amino-acid Oxidase Is Involved in D-Serine-Indused Nephrotoxicity", Chem. Res. Toxicol. 2005, 18, pp. 1678-1682.
Malkesman et al., "Acute D-serine treatment produces antidepressant-like effects in rodents", Int J Neuropsychopharmacol. Sep. 2012;15(8):1135-48.
Morel te al., "The role of glutathione and cysteine conjugates in the nephrotoxicity of o-xylene in rats", Arch Toxicol. Sep. 1993;72(9):553-8.

(Continued)

*Primary Examiner* — Maury A Audet
(74) *Attorney, Agent, or Firm* — JMB Davis Ben-David

(57) ABSTRACT

The present invention provides a pharmaceutical composition for oral administration comprising a D-amino acid combined with an antioxidant selected from the group consisting of vitamin E, vitamin C, a glutathione or a precursor thereof.

2 Claims, No Drawings

(56) References Cited

OTHER PUBLICATIONS

Orozco-Ibarra et al., "Evaluation of oxidative stress in D-serine induced nephrotoxicity" Toxicology 2007, 229, pp. 123-135.
Otte et al., "Effects of Chronic D-Serine Elevation on Animal Models of Depression and Anxiety-Related Behavior", PLoS One, Jun. 21, 2013;8(6);e67131, 11 pages.
Sacci et al., "D-amino acid oxidase inhibitors as a novel classof drugs for schizophrenia therapy", Curr Pharm Des. 2013;19(14):2499-511.
Sasaki et al., "N-methyl D-aspartate receptor co-agonist D-serine suppresses intake of high-preference food", Am J Physiol Regul Integr Comp Physiol, Jul. 8, 2015:ajpregu.00083.2015. (Epub ahead of print) 1 page.
Sastre et al., "Experimental study of the protective effect of glutathione against cisplatin-induced nephrotoxicity", Oncol Rep. 1996 Now;3(6):1149-52.
Seif et al., "D-Serine and D-Cycloserine Reduce Compulsive Alcohol Intake in Rats", Neuropsychopharmacology. Mar. 24, 2015. Doi: 10: 1038/npp.2015.84. (E-pub ahead of print). 1 page.
Soto, "D-Serine exposure resulted in gene expression changes indicative of activation of fibrogenic pathways and down-regulation of energy meatbolism and oxidative stress response", Toxicology 2008, 243, pp. 177-192.
Tsai et al., "D-alanine added to antipsychotics for the treatment of schizophrenia", Biol Psychiatry. Feb. 1, 2006;59(3):230-4.
Tsai et al., "D-serine added to antipsychotics for the treatment of schizophrenia", Biol Psychiatry, Dec. 1, 1998;44(11):1081-9.
Tsai et al., "Strategies to enhance N-methyl-D-aspartate receptor-mediated neurotransmission in schizophrenia, a critical review and meta-analysis", Curr Pharm Des. 2010;16(5):522-37.
Williams et al., "Sodium benzoate attenuates D-serine induced nephrotoxicity in the rat", Toxicology 2005, 207, pp. 35-48.
Zunino et al., "Protective effect of reduced glutathione against cis-dichlorodiammine platinum (II)-induced nephrotoxicity and lethal toxicity", Tumori. Apr. 30, 1983;69(2):105-11.
http://en.wikipedia.org/wiki/Glutathione. Last updated Dec. 19, 2014.
Azmus et al., "Effectiveness of acetylcysteine in prevention of contrast nephropathy", The Journal of Invasive Cardiology, 2005, vol. 17, pp. 80-84.
Betten et al., "A prospective evaluation of shortened course oral N-acetylcysteine for the treatment of acute acetaminophen poisoning", Annals of Emergency Medicine, 2007, vol. 50, No. 3, pp. 272-279.
Brigouri et al., "Renal insufficiency following contrast media administration trial (REMEDIAL):A randomized comparison of 3 preventive strategies", Circulation, 2007, vol. 115. pp. 1211-1217.
Dilger et al., "Oral N-acetyl-L-cysteine is a safe and effective precursor of cysteine", Journal of Animal Science, 2007, vol. 85, pp. 1712-1718.
Goldenberg et al., "Oral acetylcysteine as an adjunct to saline hydration for the prevention of contrast-induced nephropathy following coronary angiography. A randomized controlled trial and review of the current literature", European Heart Journal, 2004, vol. 25, pp. 212-218.
Kaltenbach et al., "Compounds protective against renal tubular necrosis induced by D-serine and D-2,3-diaminopropionic acid in the rat", Experimental and Molecular Pathology, 1982, vol. 37, pp. 225-234.
Lawlor et al., "Prevention of contrast-induced nephropathy in vascular surgery patients", Annals of Vascular Surgery, 2007, vol. 21, pp. 593-597.
Li et al., "Dietary supplementation with cysteine prodrugs selectively restores tissue glutathione levels and redox status in protein-malnourished mice(1)", j Nutr Biochem, 2002, vol. 13, pp. 625-633.
Muldoon et al., "Effect of N-acetylcysteine route of administration on chemoprotection against cisplatin-induced toxicity in rat models", Cancer Chemotherapy Pharmacology, 2008, vol. 62, No. 2, pp. 235-241.
Recio-Mayoral et al., "The reno-protective effect of hydration with sodium bicarbonate plus N-acetylcysteine in patients undergoing emergency precutaneous coronary intervention: The RENO study", Journal of the Americen College of Cardiology, 2007, vol. 49, No. 12, pp. 1283-1288.
Sandhu et al., "The role of N-acetylcysteine in the prevention of contrast-induced nephrotoxicity", Cardiovascular and Interventional Radiology, 2660, vol. 29, pp. 344-347.
Shalansky et al., "N-acetylcysteine for prevention of radiocontrast induced nephrotoxicity: The importance of dose and route of administration", Heart (British Cardiac Society), 2005, vol. 91, pp. 997-999.
Soto et al., "D-serine exposure resulted in gene expression changes indicative of activation of fibrogenic pathways and down-regulation of energy metabolism and oxidative stress response", Toxicology, 2008, vol. 243, issue 1-2, p. 177-192.
Stacul et al., "Strategies to reduce the risk of contrast-induced nephropathy", The Journal of Cardiology, 2006, vol. 98, 59K-77K.

* cited by examiner

PHARMACEUTICAL COMPOSITIONS AND METHODS UTILIZING A D-AMINO ACID

CROSS REFERENCE TO RELATED APPLICATIONS

This is a Continuation of co-pending U.S. patent application Ser. No. 12/350,901, filed Jan. 8, 2009, which claims the benefit of Israel Patent Application No. IL188681, filed Jan. 8, 2008. The contents of the foregoing applications are incorporated by reference herein in their entirety.

FIELD

The present invention relates to a pharmaceutical composition for treating a neuropsychiatric disorder and to methods utilizing the same.

BACKGROUND

D-serine is a naturally occurring amino acid and one of a class of amino acids that is known to be useful for treatment of neuropsychiatric disorder but which may cause nephrotoxicity when administered to rodents. In the brain, D-serine serves as a modulator of N-methyl-D-aspartate (NMDA)-type glutamate receptors. Deficiencies of D-serine or of NMDA neurotransmission may contribute to the pathophysiology of multiple neuropsychiatric disorders including schizophrenia, Alzheimers disease, attention deficit hyperactivity disorder, autism, depression, and movement disorders (Javitt 2000; Tsai 2001). It has been proposed therefore that oral administration of D-serine at doses of 1 mg-100 g may serve as a novel treatment for these disorders. Clinical use of D-serine and of similar D-amino acids is potentially limited by concerns regarding renal toxicity, which has been observed in rodent species, especially in the rat. Thus, compounds are needed that prevent nephrotoxicity when given orally along with D-serine.

The ability of D-serine to induce renal injury in rats is reviewed by (Kaltenbach et al 1979). D-serine induced nephrotoxicity has been demonstrated since at least 1942, when it was noted an injurious action of DL-serine administered by stomach tube in rats maintained on a synthetic deficient in protrain and in B vitamins. Subsequent studies demonstrated that administration of 100 mg DL-serine induced acute renal necrosis at the junction of the renal cortex and medulla which was observed when serine was added to either stock diet or diet deficient in B vitamins. Lesions were consistently produced reliable with doses as small as 5 mg D-serine per 100 g. Despite intensive investigation, the mechanism by which orally administered D-serine induces nephrotoxicity remains an area of active research.

Nephrotoxicity induced by D-serine and other related amino acids is characterized by corticomedullary pathology, such as necrosis of the straight segment of the proximal tubule in the rat kidney following oral or intravenous administration. Severity of nephrotoxicity can be monitored by assessment of serum levels of creatanine and BUN (Orozco-Ibarra et al 2007). Similar nephrotoxicity can be induced by compounds structurally related to D-serine, including D-2,3-aminopropionic acid (DAPA) (Kaltenbach et al 1979).

Wachstein et al. investigated the ability of various compounds to reverse the effects of orally administered DL-serine (100 mg) as discussed by Kaltenbach et al., (Kaltenbach et al 1982). In all cases, test compounds were administered either subcutaneously or intramuscularly. These studies showed that nephrotoxic effects of DL-serine could be blocked by either DL-methionine or glutathione (GSH) when co-injected with D-serine in rats protects against the nephrotoxicity. Other compounds showing partial or full prevention of toxicity included glycine, DL-threonine, glycolic acid and sodium lactate. Several other compounds, however, were relatively ineffective including L-cysteine, sodium thioglycollate, 2,3 dithiopropanol (BAL), DL-alpha-alanine, L-histidine, L-arginine, DL-valine, butyric acid, D-glucose, sodium chloride, and sodium acetate. It was hypothesized that beneficial effects of these compounds were due to suppression of tubular reabsorption of the D-isomer.

Subsequent studies demonstrated significant protective effects of D-alanine, D-threonine, D-homoserine, DL-alpha-methylserine, beta-hydroxy-DL-leucine, and alpha-aminoisobutryic acid. As in Wachstein, all compounds were administered by injection prior to D-serine administration (Kaltenbach et al 1982). More recently, protective effects of alpha-aminoisobutyric acid (AIB) have been confirmed. It is hypothesized that this compound prevents uptake of D-serine into renal tubular cells, thereby limiting its nephrotoxic effects (Krug et al 2007).

In general, nephrotoxic effects of D-serine are considered to result from its metabolism by D-aminoacid oxidase (DAAO), which liberates reactive oxygen species such as peroxide (Krug et al 2007; Maekawa et al 2005; Williams and Lock 2005). This theory is supported by the observation that D-serine is not nephrotoxic is rats lacking-DAAO (Maekawa et al 2005), and that toxicity can be prevented by intrarenal injection of equimolar glutathione with D-serine (Krug et al 2007) or by intraperitoneal administration of large doses of sodium benzoate (Williams and Lock 2005). However, this theory is challenged by a recent study that failed to detect increased reactive oxygen species or peroxidation markers in rat kidney following D-serine injection. Further, several compounds with an antioxidant effect failed to prevent D-serine nephrotoxicity. (Orozco-Ibarra et al 2007). Therefore, not only can it be concluded from this reference that oxidative stress alone may be an insufficient model for nephrotoxicity, but this reference also constitutes a clear teaching away from the discovery of the present invention that in fact certain antioxidants when administered together with a D-amino acid are effective for reducing the risk of nephrotoxicity.

SUMMARY

Thus, the present invention derives from the discovery that orally administered precursors of glutathione (GSH), including the compounds N-acetylcysteine and L-cysteine, prevent nephrotoxicity induced by the amino acid D-serine. The present invention provides a method for oral administration of D-serine or similar amino acids that minimizes risks of nephrotoxicity. This formulation therefore represents a significant, clinically useful improvement over use of D-serine or other amino acids alone as medicaments for neuropsychiatric or other medical conditions.

D-amino acids in general, and D-serine in specific are considered appropriate therapeutics in various neuropsychiatric conditions including schizophrenia, movement disorders, cognitive dysfunction, memory disorders and attentional disorders. Use of these compounds in clinical settings, however, is potentially limited by nephrotoxicity. In animal studies, intravenous or intraperitoneal administration of glutathione has been shown to limit toxicity induced by D-serine. However, non-oral routes of administration are not feasible for clinical treatment, necessitating alternative approaches. Oral NAC administration is a widely used treatment for hepatotoxicity, particularly following acetominophen administration (Amirzadeh and McCotter 2002; Betten et al 2007), and is equally effective to iv NAC in the majority of cases (Kanter 2006). However, oral NAC or other glutathione precursors have not been found to be effective treatments for nephrotoxicity induced by a wide variety of agents including contrast agents and chemotherapies. Despite intensive investigation of treatments that might reverse D-serine nephrotoxicity, oral NAC or other glutathione precursors have not been evaluated previously against D-serine-induced nephrotoxicity either in humans or animal models.

According to the present invention, there is now some evidence suggesting that the combination of NAC and L-cysteine (Groups B&C) are superior to either agent alone (Groups D&E) as seen in the examples here and after. No one has previously suggested using the presently suggested combined treatment, and the observed synergy is an unexpected finding.

Furthermore, as far as applicant was able to determine, the research leading to the common invention was the first study to evaluate NAC in combination with L-cysteine. The observed efficacy of both NAC and L-cysteine in the present examples is however consistent with the concept that NAC functions largely by supplying L-cysteine to the portal circulation as postulated by Dilger and Baker 2007.

More specifically, according to the present invention, there is now provided a pharmaceutical composition for oral administration comprising a D-amino acid combined with an antioxidant selected from the group consisting of vitamin E, vitamin C, a glutathione or a precursor thereof.

In preferred embodiments of the present invention the D-amino acid is selected from the group consisting of D-serine, D-alanine, D-cysteine, D-homocysteine, or D-threonine In some preferred embodiments of the present invention the antioxidant is glutathione or a precursor thereof.

In other preferred embodiments of the present invention the glutathione precursor is selected from the group consisting of L-cysteine or N-acetyl-L-cysteine and racemic versions or combinations thereof. In other preferred embodiments of the present invention the antioxidant is vitamin E while in yet other preferred embodiments the antioxidant is vitamin C.

Preferably, the D-amino acid and antioxidant are present in molar ratios of between 1:10 and 10:1.

In another aspect of the present invention, there is provided a method for treating a neuropsychiatric disorder characterized by attenuated NMDA neurotransmission comprising administering the pharmaceutical composition defined above.

In some preferred embodiments of the present invention the neuropsychiatric disorder is schizophrenia, schizophreniform disorder, psychosis NOS, or prodromal schizophrenia.

In other preferred embodiments of the present invention the neuropsychiatric disorder is Alzheimer's disease.

The present invention also provides a method for treating a neuropsychiatric disorder characterized by attenuated NMDA neurotransmission in a patient, the method comprising administering to a patient diagnosed as suffering from the neuropsychiatric disorder an oral pharmaceutical composition comprising a therapeutically effective amount of a D-amino acid combined with a an anti-oxidant selected from the group consisting of vitamin E, vitamin C, a glutathione or a precursor thereof.

Orally active compounds have been described that serve as glutathione precursors and protect the liver. In particular, N-acetylcysteine (NAC) is a glutathione prodrug that is currently approved for treatment of acetaminophen-induced hepatotoxicity (Atkuri et al 2007) and also to treat glutathione deficiency. NAC has also been evaluated as potential treatment for nephrotoxicity induced by a variety of agents, especially intravenous contrast fluid (Stacul et al 2006). At present however, no oral treatments are known that prevent oxidative damage to the kidney in response to D-serine or other potentially nephrotoxic agents.

Although the efficacy of intravenously administered NAC against nephrotoxicity has been shown repeatedly (Briguori et al 2007; Recio-Mayoral et al 2007), similar studies using oral NAC have not found benefit over hydration alone for blockade of nephrotoxicity due to intravenous contrast (Azmus et al 2005; Goldenberg et al 2004; Lawlor et al 2007; Sandhu et al 2006; Shalansky et al 2005). Previous studies have also not found beneficial effects of oral NAC against experimental nephrotoxicity induced by cisplatin in rats, although invtravenous NAC was effective (Dickey et al 2007). Further, it has previously been reported that kidney NAC levels are not increased following either acute or chronic oral administration in rat, and that NAC alone may worsen oxidative stress (Arfsten et al 2007). Other cysteine prodrugs have also been shown to be ineffective (Li et al 2002). Of note, however, no studies to date have investigated effects of orally administered glutathione precursors on D-serine-induced nephrotoxocity in vivo, or effects of N-acetylcysteine and other glutathione precursors administered in combination.

The present invention is further distinguished from prior treatments for D-amino acid-induced nephrotoxicity in that it employs oral, rather than intravenous administration of N-acetylcysteine and L-cysteine for reversal of D-serine induced nephrotoxicity, and utilizes combinations of glutathione precursors rather than administration of individual precursors alone. Despite over 60 years of research in this field, no prior studies have evaluated use of oral glutathione precursors or other anti-oxidants such as vitamin E or vitamin C against D-amino acid induced toxicity.

The invention is useful in that it permits administration of oral D-amino acids to humans with reduced risk of nephrotoxicity. D-amino acids, particularly D-serine, have proven effective for treatment of neuropsychiatric disorders. The present invention therefore provides an improved method for treatment of neuropsychiatric disorders. Other features and advantages of the invention will be apparent from the following detailed description, and from the claims.

Definitions

The term amino acid as used herein refers to amino acid is a molecule that contains both amine and carboxyl functional groups. In biochemistry, this term refers to alpha-amino acids with the general formula $H_2NCHRCOOH$, where R is an organic substituent. In the alpha amino acids, the amino and carboxylate groups are attached to the same carbon, which is called the .alpha.-carbon. The various alpha amino acids differ in which side chain (R group) is attached to their alpha carbon. They can vary in size from just a hydrogen atom in glycine, through a methyl group in alanine, to a large heterocyclic group in tryptophan.

The term anti-oxidant as used herein refers to a molecule capable of slowing or preventing the oxidation of other molecules. Oxidation is a chemical reaction that transfers electrons from a substance to an oxidizing agent. Oxidation reactions can produce free radicals, which start chain reactions that damage cells. Antioxidants terminate these chain reactions by removing free radical intermediates, and inhibit other oxidation reactions by being oxidized themselves.

Examples of antioxidants include glutathione, vitamin C, and vitamin E. The term Vitamin C refers to L-ascorbate and related molecules. The term Vitamin E refers is the general name for two classes of molecules (tocopherols and tocotrienols) having vitamin E activity in nutrition The term "neuropsychiatric disorder" as used herein refers to a disease having a pathophysiological component of attenuated NMDA receptor-mediated neurotransmission. Examples of such disorders include schizophrenia, Alzheimer's disease, autism, depression, benign forgetfulness, childhood learning disorders, close head injury, and attention deficit disorder.

The term "schizophrenia" as used herein refers to a psychiatric disorder that includes at least two of the following: delusions, hallucinations, disorganized speech, grossly disorganized or catatonic behavior, or negative symptoms. The term "schizophreniform disorder" as used herein refers to a psychiatric disorder that are identical to those of schizophrenia except for two differences: the total duration of the illness (including prodromal, active, and residual phases) is at least 1 month but less than 6 months and impaired social or occupational functioning during some part of the illness is not required (although it may occur). The term "psychosis NOS" as used herein refers to a psychiatric disorder comprising a psychosis but not meeting criteria for either schizophrenia or schizophreniform disorder. Patients can be diagnosed as having schizophrenia, schizophreniform disorder or psychosis NOS using the DSM-IV criteria (APA, 1994, Diagnostic and Statistical Manual of Mental Disorders (Fourth Edition), Washington, D.C.). The term "prodromal schizophrenia" refers to a condition in which symptoms of schizophrenia are present in attenuated form, so that full criteria for a schizophrenic disorder are not present.

The term "Alzheimer's Disease" as used herein refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease—and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141:1356-1364).

The term "autism" as used herein refers to a state of mental introversion characterized by morbid self-absorption, social failure, language delay, and stereotyped behavior. Patients can be diagnosed as suffering from autism by using the DSM-IV criteria.

The term "depression" as used herein refers to a clinical syndrome that includes a persistent sad mood or loss of interest in activities, which lasts for at least two weeks in the absence of treatment. The DSM-IV criteria can be used to diagnose patients as suffering from depression.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell, 1975, J. Consult Clin. Psychol. 43:800-809).

The term "childhood learning disorders" as used herein refers to an impaired ability to learn, as experienced by certain children. Such learning disorders can be diagnosed by using the DSM-IV criteria.

The term "closed head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to at disorder that is most commonly exhibited by children and which can be characterized by increased motor activity and a decreased attention span. The DSM-IV criteria can be used to diagnose attention deficit disorder.

The terms "D-serine" and "D-alanine" as used herein refer to the D isomers of the amino acids serine and alanine, respectively. As D isomers, rather than L isomers, these amino acids are not naturally found in proteins.

The term "nephrotoxicity" or "renal toxicity" as used herein refers to drug-induced damage to the kidney and, particularly, to necrosis of the renal tubules. Such damage may be caused by any of a number of nephrotoxic agents including aminoglycosides, cis-platinum, intravenous contrast, and D-amino acids.

The term "pharmaceutical treatment" as used herein refers to any pharmacological agent, nutritional product, micronutrient or other such agent whether or not currently approved that is used to alleviate symptoms of a neuropsychiatric disorder. Such treatments may be used either in single dose or in repeated doses over days, weeks, months, years or lifetime of an individual.

The term "glutathione" or "GSH" as used herein refers to a tripeptide comprised of the amino acids L-cysteine, L-glutamate and glycine. It contains an unusual peptide linkage between the amine group of cysteine and the carboxyl group of the glutamate side chain. It is synthesized first by combination of L-glutamate and L-cysteine to form the compound gamma-glutamylcysteine, whereafter glycine is added to the C-terminal of gamma-glutamylcysteine to form the glutatione tripeptide. N-acetyl cysteine (NAC) is an N-acetylated form of the amino acid L-cysteine that has been approved for pharmaceutical use in the USA. The term "glutathione precursor" refers to the amino acids or intermediates that participate in glutathione synthesis, or compounds that readily interconvert with such agents.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE

The example below illustrates how orally administered glutathione precursors may be used to minimize nephrotoxic effects of orally administered D-serine. Subjects consisted of Sprague Dawley rats, which are known to be sensitive to nephrotoxic effects of D-serine. Rats were divided into 5 separate groups of four male and four female animals each. The groups received the following treatments by oral gavage, in addition to standard diet:
  Group A: D-serine alone;
  Group B: D-serine, L-cysteine and N-acetylcysteine in a ratio of 4:3:1;
  Group C: D-serine, L-cysteine and N-acetylcysteine in a ratio of 2:1:1;
  Group D: D-serine, L-cysteine and N-acetylcysteine in a ratio of 1:0:1; and
  Group E: D-serine, L-cysteine and N-acetylcysteine in a ratio of 1:1:0.

In addition, a control group received only standard diet. Compounds A, B, C, D & E were administered by single oral gavage at the doses of 50 mg/kg, 100 mg/kg, 200 mg/kg & 400 mg/kg body weight and at the dose volume of 5 ml/kg. Effects of various doses were investigated in a sequential manner starting with 50 mg/kg. Dose level was doubled every three days up to four doses (50 mg, 100 mg, 200 mg & 400 mg).

During the study, no significant mortality was observed in any group. All animals survived until study termination. Further, all animals were free of clinical abnormalities up to the dose of 400 mg/kg.

Nephrotoxicity was assessed in two ways: first, by creatanine levels and second by histophathology at necropsy.

Creatanine levels during D-serine treatment are shown in Table 1. Both control and D-serine alone groups showed a significant increase in creatanine levels during chronic treatment, as did Groups B and C, but not groups D (D-serine+N-acetylcysteine) and E (D-serine+L-cysteine). For all experimental groups (Groups B-E), the degree of increase in creatanine during treatment with combined treatment was significantly less than during treatment with D-serine alone. Further, for both groups D and E, the degree of increase in creatanine level was significantly less than for the control group. The degree of creatanine increase during treatment was small in both groups D and E and did not differ significantly between these two treatments. These findings indicate that L-cysteine and NAC, alone or in combination, significantly reduce levels of creatanine increase seen with D-serine treatment alone.

Potential nephrotoxic effects of D-serine alone or in combination with L-cysteine or N-acetylcysteine were also evaluated by histopathological examination at necropsy. The kidney section in these studies showed features of early tubular nephrosis changes, especially involving the tubular structure of medullary and corticomedullary junction when compared with the kidney section of control animals, indicating early nephrotoxic changes induced by the test compounds. The mean severity grade of tubular nephrosis across compounds is show in Table 2, with the D-serine group showing a mean nephrosis grade of 1.91 (mild). Both the 4:3:1 (Group B) and 2:1:1 (Group C) combinations of D-serine, L-cysteine and N-acetylcysteine showed reduced nephrosis ratings compared to D-serine alone, although nephrosis ratings with combined D-serine and L-cysteine (Group D) alone or combined D-serine and N-acetylcysteine alone (Group E) were slightly higher than those with D-serine alone (Group A).

Taken together, these findings indicate that a 2:1:1 ratio of D-serine:L-cysteine:N-acetylcysteine produces both decreased rise in creatanine and also less evidence of histopathological evidence of nephrotoxicity vs. D-serine alone, and thus represents a preferential oral formulation. Other combinations also show superiority in either the creatanine or hydronephrosis assay with no significant inferiority in either assay and thus may also be used as embodiments of this invention.

TABLE 2

Table 2: Results of histopathological examination

| Group | Compostion and ratio | Nephrosis level |
|---|---|---|
| Control | Vehicle Control (Water) | |
| A | D-serine alone | 1.91 |
| B | D-serine + L-cysteine + N-acetylcysteine (4:3:1) | 1.00 |
| C | D-serine + L-cysteine + N-acetylcysteine (2:1:1) | 1.33 |
| D | D-serine + L-cysteine + N-acetylcysteine (1:0:1) | 2.00 |
| E | D-serine + L-cysteine + N-acetylcysteine (1:1:0) | 2.00 |

DETAILED DESCRIPTION

The invention describes a method for reducing risk of nephrotoxicity during oral treatment with a D-amino acid, comprising a composition containing a D-amino acid combined with an orally active antioxidant. The invention also describes an improved method for treating a patient diagnosed as suffering from a neuropsychiatric disorder having a deficit in neurotransmission via the NMDA receptor, for whom D-serine treatment might be desirable. The present invention has the advantage of decreasing risk of nephrotoxicity during treatment with D-serine or other neuropsychiatric illness.

TABLE 1

| Group Assignment | Ratio D-ser: L-cyst: N-acetylcyst | Pre-treatment Mean | Pre-treatment stdev | Post-treatment mean | Post-treatment stdev | Change mean | Change stdev | T-test post vs. pre | T-test vs. D-ser alone |
|---|---|---|---|---|---|---|---|---|---|
| Control | Control | 0.67 | 0.03 | 0.77 | 0.06 | 0.10 | 0.08 | 0.01 | |
| A | D-serine alone (1:0:0) | 0.65 | 0.03 | 0.77 | 0.02 | 0.12 | 0.04 | 0.00 | |
| B | 4:3:1 | 0.65 | 0.03 | 0.74 | 0.03 | 0.10 | 0.03 | 0.00 | 0.0406 |
| C | 2:1:1 | 0.65 | 0.02 | 0.72 | 0.04 | 0.07 | 0.04 | 0.01 | 0.0111 |
| D | 1:0:1 | 0.65 | 0.02 | 0.69 | 0.02 | 0.04 | 0.03 | 0.22 | 0.0000 |
| E | 1:1:0 | 0.64 | 0.04 | 0.68 | 0.05 | 0.04 | 0.06 | 0.92 | 0.0003 |

The treatment method of the invention entails administering to a patient diagnosed as having a neuropsychiatric disorder an oral pharmaceutical composition containing a therapeutically effective amount of (i) a D-amino acid including but not limited to D-serine, and (ii) an orally effective anti-oxidant, including but not limited to glutathione, N-acetylcysteine, L-cysteine or glutathione precursors. D-amino acids, glutathione and glutathione precursors are commercially available (e.g. Sigma Chemicals, St. Louis, Mo.)

Typically, in this invention, the antioxidant is given in molar ratios of 10:1 to 1:10 with the D-amino acid, with preferred embodiments having ratios of between 4:1 and 1:1. Typically, the D-amino acid is given in doses of 1 g/d-100 g/d. A typical implementation of this invention, therefore, would be to administer a formulation consisting of 8 g D-serine and 2 g N-aceyticysteine, L-cysteine or a combination thereof in 1-3 daily divided doses. In all of the methods of the invention, glutathione or glutathione precursors can be combined with or replaced with the antioxidants vitamin E or vitamin C.

In all of the methods of the invention, appropriate dosages of D-amino acids combined with NAC, L-cysteine or other NAC precursors can readily be determined by those of ordinary skill in the art of medicine by monitoring the patient for signs of disease amelioration or inhibition, and increasing or decreasing the dosage and/or frequency of treatment as desired.

The pharmaceutical compositions can be administered to the patient by any, or a combination, of several routes other than intravenous or intramuscular, such as oral, trans-mucosal (e.g., nasal, vaginal, etc.), pulmonary, transdermal, ocular, buccal, or sublingual. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Alternatively, the pharmaceutical composition can be formulated as a chewing gum, lollipop, or the like.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

LITERATURE CITED

Amirzadeh A, McCotter C (2002): The intravenous use of oral acetylcysteine (mucomyst) for the treatment of acetaminophen overdose. Archives of internal medicine 162: 96-97.

Arfsten D P, Johnson E W, Wilfong E R, Jung A E, Bobb A J (2007): Distribution of radio-labeled N-Acetyl-L-Cysteine in Sprague-Dawley rats and its effect on glutathione metabolism following single and repeat dosing by oral gavage. Cutaneous and ocular toxicology 26:113-134.

Atkuri K R, Mantovani J J, Herzenberg L A, Herzenberg L A (2007): N-Acetylcysteine—a safe antidote for cysteine/glutathione deficiency. Current opinion in pharmacology 7:355-359.

Azmus A D, Gottschall C, Manica A, Manica J, Duro K, Frey M, et al (2005): Effectiveness of acetylcysteine in prevention of contrast nephropathy. The Journal of invasive cardiology 17:80-84.

Betten D P, Cantrell F L, Thomas S C, Williams S R, Clark R F (2007): A prospective evaluation of shortened course oral N-acetylcysteine for the treatment of acute acetaminophen poisoning. Annals of emergency medicine 50:272-279.

Briguori C, Airoldi F, D'Andrea D, Bonizzoni E, Morici N, Focaccio A, et al (2007): Renal Insufficiency Following Contrast Media Administration Trial (REMEDIAL): a randomized comparison of 3 preventive strategies. Circulation 115:1211-1217.

Dickey D T, Muldoon L L, Doolittle N D, Peterson D R, Kraemer D F, Neuwelt E A (2007): Effect of N-acetylcysteine route of administration on chemoprotection against cisplatin-induced toxicity in rat models. Cancer Chemother Pharmacol.

Dilger R N, Baker D H (2007): Oral N-acetyl-L-cysteine is a safe and effective precursor of cysteine. Journal of animal science 85:1712-1718.

Goldenberg I, Shechter M, Matetzky S, Jonas M, Adam M, Pres H, et al (2004): Oral acetylcysteine as an adjunct to saline hydration for the prevention of contrast-induced nephropathy following coronary angiography. A randomized controlled trial and review of the current literature. European heart journal 25:212-218.

Javitt D C (2000): Treatment of negative and cognitive symptoms with D-serine. In: USPTO editor. USA.

Kaltenbach J P, Carone F A, Ganote C E (1982): Compounds protective against renal tubular necrosis induced by D-serine and D-2,3-diaminopropionic acid in the rat. Experimental and molecular pathology 37:225-234.

Kaltenbach J P, Ganote C E, Carone F A (1979): Renal tubular necrosis induced by compounds structurally related to D-serine. Exp Molec Pathol 30:209-214.

Kanter M Z (2006): Comparison of oral and i.v. acetylcysteine in the treatment of acetaminophen poisoning. Am J Health Syst Pharm 63:1821-1827.

Krug A W, Volker K, Dantzler W H, Silbernagl S (2007): Why is D-serine nephrotoxic and alpha-aminoisobutyric acid protective? American journal of physiology 293: F382-390.

Lawlor D K, Moist L, DeRose G, Harris K A, Lovell M B, Kribs S W, et al (2007): Prevention of contrast-induced nephropathy in vascular surgery patients. Annals of vascular surgery 21:593-597.

Li J, Wang H, Stoner G D, Bray T M (2002): Dietary supplementation with cysteine prodrugs selectively restores tissue glutathione levels and redox status in protein-malnourished mice(1). J Nutr Biochem 13:625-633.

Maekawa M, Okamura T, Kasai N, Hori Y, Summer K H, Konno R (2005): D-amino-acid oxidase is involved in D-serine-induced nephrotoxicity. Chemical research in toxicology 18:1678-1682.

Orozco-Ibarra M, Medina-Campos O N, Sanchez-Gonzalez D J, Martinez-Martinez C M, Floriano-Sanchez E, Santamaria A, et al (2007): Evaluation of oxidative stress in D-serine induced nephrotoxicity. Toxicology 229:123-135.

Recio-Mayoral A, Chaparro M, Prado B, Cozar R, Mendez I, Banerjee D, et al (2007): The reno-protective effect of hydration with sodium bicarbonate plus N-acetylcysteine in patients undergoing emergency percutaneous coronary intervention: the RENO Study. Journal of the American College of Cardiology 49:1283-1288.

Sandhu C, Belli A M, Oliveira D B (2006): The role of N-acetylcysteine in the prevention of contrast-induced nephrotoxicity. Cardiovascular and interventional radiology 29:344-347.

Shalansky S J, Pate G E, Levin A, Webb J G (2005): N-acetylcysteine for prevention of radiocontrast induced nephrotoxicity: the importance of dose and route of administration. Heart (British Cardiac Society) 91:997-999.

Stacul F, Adam A, Becker C R, Davidson C, Lameire N, McCullough P A, et al (2006): Strategies to reduce the risk of contrast-induced nephropathy. The American journal of cardiology 98:59K-77K.

Tsai G E (2001): Methods for treating neuropsychiatric disorders.

Williams R E, Lock E A (2005): Sodium benzoate attenuates D-serine induced nephrotoxicity in the rat. Toxicology 207:35-48.

I claim:

1. A method for treating a neuropsychiatric disorder characterized by attenuated NMDA neurotransmission in a patient in need thereof by treatment with D-serine, but with reduced D-serine associated nephrotoxicity, the method comprising administering orally to the patient a therapeutically effective amount of D-serine combined with L-cysteine and N-acetyl-L-cysteine in a ratio of 2:1:1 to 4:3:1.

2. The method of claim 1, wherein the neuropsychiatric disorder is schizophrenia.

* * * * *